United States Patent [19]

Kline

[11] 4,108,830
[45] Aug. 22, 1978

[54] SULFUR-CONTAINING PHENOLIC ANTIOXIDANTS

[75] Inventor: Richard H. Kline, Cuyahoga Falls, Ohio

[73] Assignee: The Goodyear Tire & Rubber Company, Akron, Ohio

[21] Appl. No.: 672,105

[22] Filed: Mar. 31, 1976

Related U.S. Application Data

[63] Continuation-in-part of Ser. No. 597,804, Jul. 21, 1975, abandoned.

[51] Int. Cl.² .................... C07C 69/34; C07C 69/74; C07C 69/76; C07C 103/19; C07C 103/24; C08R 5/36

[52] U.S. Cl. .................... 260/45.85 S; 260/45.9 NC; 260/557 R; 260/561 S; 260/562 P; 260/562 A; 260/558 S; 560/18; 560/9

[58] Field of Search .............. 260/45.85 S, 468 H, 260/468 J, 479 S, 475 SC, 481 R, 45.9 NC, 557 R, 561 S, 562 P, 562 A, 558 S

[56] References Cited

U.S. PATENT DOCUMENTS

| | | | |
|---|---|---|---|
| 3,247,240 | 4/1966 | Meier | 260/45.9 NC |
| 3,459,704 | 8/1969 | Peterson et al. | 260/45.85 T |
| 3,637,809 | 1/1972 | Kleiner | 260/479 S |
| 3,679,744 | 7/1972 | Knell et al. | 260/45.9 NC |
| 3,780,103 | 12/1973 | Knell | 260/45.9 NC |
| 3,927,091 | 12/1975 | Huber-Emden et al. | 260/45.9 NC |
| 3,935,161 | 1/1976 | Schlichting et al. | 260/45.9 NC |

FOREIGN PATENT DOCUMENTS

1,241,617 8/1971 United Kingdom.

*Primary Examiner*—V. P. Hoke
*Attorney, Agent, or Firm*—J. A. Rozmajzl

[57] ABSTRACT

Phenolic antioxidants such as bis(3,5-di tert.butyl-4-hydroxyphenyl) 2,9-dimethyl-4,7-dithiadecanedioate are used to stabilize diene rubbers such as butadiene-styrene copolymers (SBR) and polyolefins such as polypropylene.

8 Claims, No Drawings

SULFUR-CONTAINING PHENOLIC ANTIOXIDANTS

This application is a continuation-in-part of application Ser. No. 597,804 filed July 21, 1975, now abandoned.

This invention relates to the use of sulfur containing phenolic compounds as antioxidants for polymers, both saturated and unsaturated, vulcanized and unvulcanized. It also relates to a process of preparing said compounds.

Those concerned with the stabilization of polymers against oxidative degradation are constantly searching for new and effective antioxidants. In any application it is desirable that the antioxidant have a reduced tendency to discolor the polymer either before or after the polymer has been subjected to aging conditions particularly of the high temperature type. Resistance to oxidation and discoloration are extremely important in many applications in which polypropylene is used.

Those skilled in the art have used phenolic compounds on occasion to provide antioxidant protection. Some have used sulfur containing bisphenols, e.g., see U.S. Pat. Nos. 3,459,704; 3,679,744; 3,637,809 and Canadian Pat. No. 812,262.

It is an object of the present invention to provide phenolic antioxidants for the protection of polymers against oxidative degradation. Another object is to provide polymers stabilized against oxidative degradation. Still another object is to provide a process of preparing said antioxidants. Other objects will become apparent as the description proceeds.

The objects of the present invention are accomplished by the preparation and use as antioxidants in diene rubber of sulfur containing phenolic compounds having the following structural formula:

$$AXA^1$$

wherein A and $A^1$ are selected from structures I and II as follows:

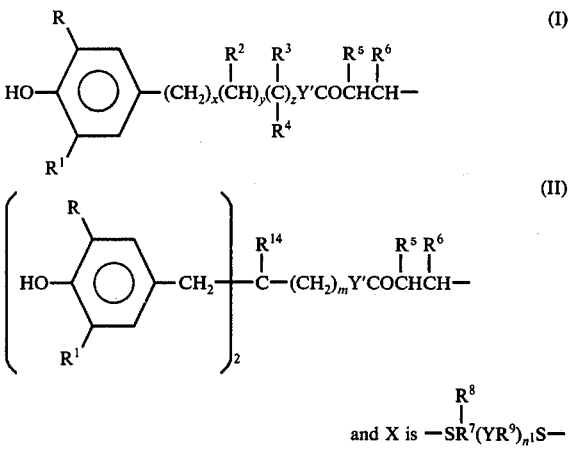

and X is $-SR^7(YR^9)_{n^1}S-$ wherein Y' is —O— or —NH— and wherein R and $R^1$ are selected from the group consisting of tertiary alkyl radicals having 4 to 8 carbon atoms and cycloalkyl radicals having 5 to 12 carbon atoms, $R^2$, $R^3$, $R^4$, $R^5$, $R^6$ and $R^8$ are selected from the group consisting of hydrogen and alkyl radicals having from 1 to 4 carbon atoms, $R^7$ is selected from the group consisting of alkylene radicals having 2 to 6 carbon atoms, cycloalkylene radicals having 5 to 12 carbon atoms and alkyl cycloalkylene radicals having the following structural formula $$-R^{11}-R^{10}-[R^{12}]_{n^2}-$$

wherein $R^9$ is an alkylene radical having 2 to 6 carbon atoms, Y is selected from the group consisting of —O—, —S—, 1,4-phenylene and

and wherein $n^1$ is 0 or 1, $x+y+z$ is 0 or a whole number from 2 to 12, $R^{10}$ is a cycloalkylene radical having from 5 to 12 carbon atoms, $R^{11}$ and $R^{12}$ are alkylene radicals having from 1 to 6 carbon atoms and $n^2$ is 0 or 1, and wherein $R^{13}$ is an alkylene radical having from 2 to 6 carbon atoms which can be substituted or unsubstituted with one or two groups of the structure

wherein B conforms to structural formula $$\begin{array}{c} R^8 \\ | \\ ASR^7- \end{array}$$

and wherein $R^{14}$ is selected from the group consisting of alkyl radicals having 1 to 4 carbon atoms and phenyl and m is 0 or 1 with the proviso that when Y' is —O—, m is 1.

Preferably R and $R^1$ are tert.butyl radicals, $R^2$, $R^3$, $R^4$, $R^5$ and $R^8$ are hydrogen or methyl, $R^6$ is hydrogen, $R^7$ and $R^9$ are ethylene, $n^1$ is 0, x is 0 to 3, y is 0 or 1, z is 0 or 1, and $x+y+z$ is 0, 2 or 3. Preferably $R^{10}$ is cyclohexyl, $R^{11}$ is ethylene and $n^2$ is 0.

The following compounds illustrate, but do not limit, the compounds of the present invention.

| Compound No. | |
|---|---|
| I | bis(3,5-di-t-butyl-4-hydroxyphenyl) 4,10-dithia-7-oxatridecanedioate |
| II | bis(3,5-di-t-butyl-4-hydroxyphenyl) 4,7,10-trithiatridecanedioate |
| III | bis[2,2-dimethyl-3-(3,5-di-t-butyl-4-hydroxyphenyl)propyl] 4,7,10-trithia-2,12-dimethyltridecanedioate |
| IV | bis[2,2-dimethyl-3-(3,5-di-t-butyl-4-hydroxyphenyl)propyl] 4,10-dithia-7-oxa-2,12-dimethyltridecanedioate |
| V | N,N'-bis[1,1-dimethyl-2-(3,5-di-t-butyl-4-hydroxyphenyl)ethyl]-4,10-dithia-7-oxatridecanediamide |
| VI | N,N'-bis[1,1-dimethyl-2-(3,5-di-t-butyl-4-hydroxyphenyl)ethyl]-4,7-dithia-5-methyldecanediamide |
| VII | bis(3,5-di-t-butyl-4-hydroxyphenyl) 4,7-dithia-2,9-dimethyldecanedioate |
| VIII | bis(3,5-di-t-butyl-4-hydroxyphenyl) 4,7-dithia-2,5,9-trimethyldecanedioate |
| IX | bis[4-(3,5-di-t-butyl-4-hydroxyphenyl)-2-butyl] 4,7,10-trithia-2,12-dimethyltridecanedioate |
| X | bis[4-(3,5-di-t-butyl-4-hydroxyphenyl)-2-butyl] 4,7-dithia-2,9-dimethyldecanedioate |
| XI | bis[4-(3,5-di-t-butyl-4-hydroxyphenyl)-2-butyl] 4,7-dithiadecanedioate |
| XII | bis[2,2-dimethyl-3(3,5-di-t-butyl-4-hydroxyphenyl)propyl] 4,7-dithia-2,9-dimethyldecanedioate |
| XIII | bis[2,2-dimethyl-3(3,5-di-t-butyl-4-hydroxyphenyl)propyl] 4,7-dithiadecanedioate |
| XIV | bis[2,2-bis(3,5-di-t-butyl-4-hydroxybenzyl)propyl] 4,7-dithiadecanedioate |
| XV | bis[2,2-bis(3,5-di-t-butyl-4-hydroxybenzyl)butyl] 4,7-dithiadecanedioate |

| Compound No. | |
|---|---|
| XVI | 1,1,1-tris[methylene 6-(3,5-di-t-butyl-4-hydroxyphenoxycarbonyl)-4-thiahexanoate] propane |
| XVII | 1,1,1-tris[methylene 6-(3-(3,5-di-butyl-4-hydroxyphenyl)-2,2-dimethyl propoxycarbonyl]-4-thiahexanoate] propane |
| XVIII | tetrakis[methylene 6-(3,5-di-t-butyl-4-hydroxyphenoxycarbonyl)-4-thiahexanoate] methane |
| XIX | tetrakis[methylene-6-(3-(3,5-di-t-butyl-4-hydroxyphenyl)-2,2-dimethyl propoxycarbonyl]-4-thiahexanoate] methane |

All of the above compounds I to IX have been prepared. Compounds I to IV are the compounds of working examples 1 to 4.

Additional compounds which illustrate but do not limit the compounds of the present invention are as follows.

N,N'-bis(3,5-di-t-butyl-4-hydroxyphenyl)4,9-dithiadodecanediamide bis[3-(3,5-di-t-butyl-4-hydroxyphenyl)propyl] 3,3'-(1,5-cyclooctanedithio)dipropionate bis(3,5-di-t-butyl-4-hydroxyphenyl) 3,3'-[3,8-tricyclo(5.2.1.0$^{2,6}$)decanedithio]dipropionate bis[2-(3,5-di-t-butyl-4-hydroxyphenyl)ethyl] 6,6'-(1,4-phenylene)bis(4-thiahexanoate)

N,N'-bis[1-methyl-2-(3,5-di-t-butyl-4-hydroxyphenyl) ethyl]-4,7-dithia-3,8-dimethyldecanediamide 1,6-hexanediyl bis[6-(3,5-di-t-butyl-4-hydroxyphenoxycarbonyl)-4-thiahexanoate]

bis[3,5-bis(1,1-dimethylpropyl)-4-hydroxyphenyl] 4,7-dithiadecanedioate bis[2,2-bis(3,5-di-t-butyl-4-hydroxybenzyl)-2-phenylethyl]-4,7-dithiadecanedioate N,N'-bis[1,1-bis(3,5-di-t-butyl-4-hydroxybenzyl)ethyl]-4,7-dithiadecanediamide The compounds of this invention can be prepared by the base catalyzed addition of a polymercaptan to a 3,5-di tert.alkyl-4-hydroxyphenylalkyl ester or amide of an α-β unsaturated carboxylic acid. The reaction is normally carried out using an inert solvent at a temperature ranging from room temperature to the boiling point of the solvent. Their method of preparation is not critical to their use as antioxidants.

The following examples illustrate the preparation of the antioxidants of the present invention by the process of the present invention and are not intended to be limiting.

EXAMPLE 1

Bis(3,5-di-tert.butyl-4-hydroxyphenyl) 4,10-dithia-7-oxatridecanedioate (R,R'=tert.butyl; $x,y,z$=0; $R^5,R^6,R^8$=H; $R^7,R^9$=C$_2$H$_4$; Y=O; n'=1)

To a solution of 11 grams of 3,5-di-tert.butyl-4-hydroxyphenyl acrylate and 2.74 grams of 2-mercaptoethyl ether in 75 milliliters of ethanol was added 1 milliliter of triethylamine. The temperature rose from 26° C. to 31° C. over a period of several minutes and the mixture was stirred for several hours before being poured into water. The viscous oil which precipitated was separated by extraction with benzene. The benzene was evaporated leaving 13 grams of a viscous yellow oil.

EXAMPLE 2

When 3.1 grams of 2-mercaptoethyl sulfide were substituted for the 2-mercaptoethyl ether in Example 1, there was obtained 14 grams of bis(3,5-di-tert.butyl-4-hydroxyphenyl) 4,7,10-trithiatridecanedioate; also a viscous oil. (R,R'=tert.butyl; $x,y,z$=0; $R^5,R^6,R^8$=H; $R^7,R^9$=C$_2$H$_4$; Y=S; n'=1)

EXAMPLE 3

Bis[2,2-dimethyl-3-(3,5-di tert.butyl-4-hydroxyphenyl)4,7,10-trithia-2,12-dimethyltridecanedioate To a solution of 18 grams of 2,2-dimethyl-3-(3,5-di tert.butyl-4-hydroxyphenyl)propyl methacrylate and 3.85 grams of 2-mercaptoethyl sulfide in 75 milliliters of ethanol was added a solution of 1 gram of potassium hydroxide in 10 milliliters of ethanol. The temperature rose from 24° C. to 32° C. over a period of several minutes and the reaction mixture was stirred for 3 hours before being poured into water. The viscous oil which precipitated was separated by extraction with hexane and the extract was evaporated leaving 17 grams of a viscous oil which slowly crystallized on standing.

EXAMPLE 4

The substitution of 3.46 grams of 2-mercaptoethyl ether for the 2-mercaptoethyl sulfide in Example 3 yielded 19.5 grams of bis[2,2-dimethyl-3-(3,5-di-tert.butyl-4-hydroxyphenyl)propyl] 4,10-dithia-7-oxa-2,12-dimethyltridecanedioate. (R,R'= tert.butyl; $x$=2; $y$=0; $z$=1; $R^3$, $R^4$, $R^5$=CH$_3$; $R^6$, $R^8$=H; $R^7,R^9$=C$_2$H$_4$; Y=0; n'=1)

EXAMPLE 5

A mixture of 30 grams of sodium hydroxide, 5 grams of tetrabutylammonium bromide, 60 milliliters of water and 250 milliliters of benzene is heated to 70° C. and to it is added over a period of 5 hours a solution of 127.5 grams of 3,5-di-t-butyl-4-hydroxybenzyl chloride and 17.5 grams of propionaldehyde in 125 milliliters of benzene. The reaction mixture is stirred for an additional 30 minutes at 70° C. and is then neutralized by the addition of a solution of 50 milliliters of concentrated hydrochloric acid in 100 milliliters of water. The layers are separated and benzene is removed from the organic layer on a rotary evaporator. The viscous residue crystallizes on mixing with hexane and the solid is separated by filtration. There is obtained 67.5 grams of 2,2-bis(3,5-ditert.butyl-4-hydroxybenzyl propionaldehyde.

The product of the previous reaction is dissolved in 300 milliliters of ethanol and 2.6 grams of sodium borohydride is added to the solution over a period of 10 minutes. The reaction mixture is stirred for 3 hours and excess sodium borohydride is then neutralized by the addition of 10 milliliters of dilute (3:1) hydrochloric acid. The mixture is filtered and the filtrate is poured in into water. An amorphous mass precipitates from which the water is decanted. The sticky mass is dissolved in boiling hexane. The 2,2-bis(3,5-ditert.butyl-4-hydroxybenzyl)propanol crystallizes on cooling the solution and is filtered off. The product weighs 53.4 grams and melts at 162°–164° C.

5.6 grams of acryloyl chloride is added dropwise to a solution of 24.8 grams of 2,2-bis(3,5-ditert.butyl-4-hydroxybenzyl) propanol and 10 grams of triethylamine in 100 milliliters of tetrahydrofuran. Temperature during the addition rises from 25° C. to 52° C. The reaction mixture is stirred for 4½ hours and is then poured into water. The mixture is stirred until the oil which precipitates has crystallized. The product is filtered off and allowed to dry. There is obtained 27 grams of 2,2- bis(3,5-ditert.butyl-4-hydroxybenzyl) propyl acrylate which melts at 175°–179° C.

The product of the previous reaction is dissolved in 100 millilters of ethanol along with 2.3 grams of ethanedithiol and 1 milliliter of a 40% solution of benzyltrimethylammonium hydroxide in methanol. This mixture is heated under reflux for 5 hours and is then allowed to cool. The solid which has precipitated during the heating period is filtered off. There is obtained 19.3 grams of bis[2,2-bis(3,5-ditert.butyl-4-hydroxybenzyl)propyl]4,7-dithiadecanedioate which melts at 156°–161° C.

The polymers that may be conveniently protected by the compounds described herein are vulcanized and unvulcanized polymers susceptible to oxygen degradation, such as natural rubber, balata, gutta percha and synthetic polymers, both saturated and unsaturated, i.e., containing carbon to carbon double bonds. Representative examples of the synthetic polymers used in the practice of this invention are polychloroprene; homopolymers of a conjugated 1,3-diene such as isoprene and butadiene as well as copolymers of conjugated 1,3-dienes such as isoprene and butadiene with up to 40 percent by weight of at least one copolymerizable monomer such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or not unsaturation, such as polyethylene, polypropylene, ethylene propylene copolymers and terpolymers of ethylene, propylene and a nonconjugated diene.

The precise amount of the antioxidant which is to be employed will depend somewhat on the nature of the polymer and the severity of the deteriorating conditions to which the polymer is to be exposed. In unsaturated polymers such as those made from conjugated dienes, the amount of antioxidant necessary is greater than that required by a saturated polymer such as polyethylene.

Generally the stabilizers of this invention are employed in antioxidant amounts from about 0.0005 part to about 10 parts by weight per 100 parts by weight of polymer, although this will vary with the particular polymer. A particularly advantageous range is from about 0.025 part to about 1.5 parts. The compounds are especially useful for the stabilization of polyethylene and polypropylene. The antioxidants of the present invention have a high molecular weight which makes them less volatile and less easily extracted from the polymer than lower molecular weight antioxidants.

The antioxidants are effective whether used alone or in the presence of other compounding ingredients. Representative examples of such ingredients are metal oxides, reinforcing agents, pigments, fillers, softening agents, other antioxidants, plasticizing agents, curing agents and the like.

The antioxidants of the present invention can be added to the polymer in any of the conventional ways, for example by addition to the latex or solution form of the polymer or by direct addition to the polymer in solid form on a mill or in a banbury.

Compounds I, II, and IV to XIX were evaluated in SBR at the 1.0 part level. Compounds IV to IX and XII were evaluated in polypropylene. The results are listed below.

| Compound Number | Days to Failure at 140° C. in Polypropylene | Hours to Absorb 1% Oxygen at 100° C. in SBR-1006 | |
|---|---|---|---|
| I    | —  | 494 | (464) |
| II   | —  | 523 | " |
| III  | —  | —   | — |
| IV   | 22 | 536 | (464) |
| V    | 28 | 436 | (328) |
| VI   | 30 | 468 | " |
| VII  | 91 | 593 | " |
| VIII | 77 | 579 | " |
| IX   | 46 | 653 | " |
| X    | —  | 549 | (282) |
| XI   | —  | 481 | " |
| XII  | 43 | 701 | (328) |
| XIII | —  | 434 | (282) |
| XIV  | —  | 362 | (237) |
| XV   | —  | 371 | (237) |
| XVI  | —  | 375 | (280) |
| XVII | —  | 371 | " |
| XVIII| —  | 340 | " |
| XIX  | —  | 438 | " |

Figure in ( ) is for oxygen absorption value for a butylated, octylated phenolic antioxidant control.

All of the compounds tested improved the resistance of the polypropylene and SBR to degradation. Had no antioxidant been present, the polypropylene would have failed in 1 to 2 days, and the SBR would have absorbed 1.0% O₂ in 5 to 10 hours.

Any of the phenolic antioxidants described herein could be used in the previously described working examples to provide protection for any of the polymers described herein.

While certain representative embodiments and details have been shown for the purpose of illustrating the invention, it will be apparent to those skilled in this art that various changes and modifications may be made therein without departing from the spirit or scope of the invention.

What I claim is:

1. A compound having the following structural formula: $AXA^1$ wherein A and $A^1$ are selected from structures I and II as follows:

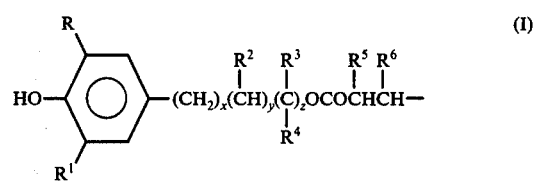

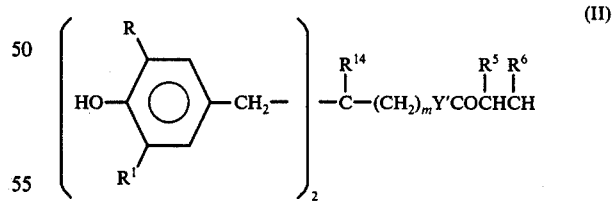

and X is

wherein Y' is —O— or —NH— and wherein R and $R^1$ are selected from the group consisting of tertiary alkyl radicals having 4 to 8 carbon atoms and cycloalkyl radicals having 5 to 12 carbon atoms, $R^2$, $R^3$, $R^4$, $R^5$, $R^6$ and $R^8$ are selected from the group consisting of hydrogen and alkyl radicals having from 1 to 4 carbon atoms, $R^7$ is selected from the group consisting of alkylene radicals having 2 to 6 carbon atoms, cycloalkylene radicals having 5 to 12 carbon atoms and alkyl cycloalkylene radicals having the structural formula $-R^{11}-R^{10}-[R^{12}]_{n^2}-$, wherein $R^9$ is an alkylene radical having 2 to 6 carbon atoms, Y is selected from the group consisting of $-O-$, $-S-$, 1,4 phenylene and $$-\underset{\underset{O}{\|}}{C}R^{13}O\underset{\underset{O}{\|}}{C}-$$

and wherein $n^1$ is 0 or 1, $x+y+z$ is 0 or a whole number from 2 to 12, $R^{10}$ is a cycloalkylene radical having from 5 to 12 carbon atoms, $R^{11}$ and $R^{12}$ are alkylene radicals having from 1 to 6 carbon atoms and $n^2$ is 0 or 1, and wherein $R^{13}$ is an alkylene radical having from 2 to 6 carbon atoms which can be substituted or unsubstituted with one or two groups of the structure $$-O\underset{\underset{}{}}{\overset{\overset{O}{\|}}{C}}B$$

wherein B conforms to structural formula $$A\underset{\underset{}{}}{\overset{\overset{R^8}{|}}{S}}R^7$$

and wherein $R^{14}$ is selected from the group consisting of alkyl radicals having 1 to 4 carbon atoms and phenyl and m is 0 or 1 with the proviso that when Y' is $-O-$, m is 1.

2. The compound of claim 1 where A and $A^1$ have a structure according to I and where Y is $$-\underset{\underset{O}{\|}}{C}-O-R^{13}-O-\underset{\underset{O}{\|}}{C}-$$

3. The compound according to claim 1 wherein A and $A^1$ have a structure according to structure I.

4. The compound according to claim 3 wherein R and $R^1$ are tert.butyl radicals, $R^2$, $R^3$, $R^4$, $R^5$ and $R^8$ are hydrogen or methyl, $R^6$ is hydrogen, $R^7$ is ethylene, $n^1$ is 0, $x$ is 0 to 3, $y$ is 0 or 1, $z$ is 0 or 1, and $x+y+z$ is 0, 2 or 3.

5. The compound according to claim 1 wherein A and $A^1$ have structural according to structure II.

6. The compound according to claim 5 wherein R and $R^1$ are tert.butyl radicals, $R^5$ and $R^8$ are hydrogen or methyl, $R^6$ is hydrogen, $R^7$ is ethylene and $R^9$ is ethylene or $n^1$ is 0.

7. A polymer prepared from ethylenically unsaturated monomers having incorporated therein a compound according to claim 1.

8. The polymer according to claim 7 wherein the polymer is selected from the group consisting of natural rubber, homopolymers of conjugated 1,3-diene, copolymers wherein at least one of the comonomers is conjugated 1,3-diene, polyurethanes containing carbon to carbon double bonds, polyethylene, polypropylene, ethylene-propylene copolymers and terpolymers of ethylene, propylene and a nonconjugated diene.

* * * * *